(12) United States Patent
Fine

(10) Patent No.: US 8,277,384 B2
(45) Date of Patent: Oct. 2, 2012

(54) SYSTEM AND METHOD FOR IN VIVO MEASUREMENT OF BIOLOGICAL PARAMETERS

(75) Inventor: Ilya Fine, Rehovot (IL)

(73) Assignee: Ilya Fine, Rehovot (IL)

( * ) Notice: Subject to any disclaimer, the term of this patent is extended or adjusted under 35 U.S.C. 154(b) by 626 days.

(21) Appl. No.: 12/431,469

(22) Filed: Apr. 28, 2009

(65) Prior Publication Data

US 2009/0209834 A1 Aug. 20, 2009

Related U.S. Application Data

(63) Continuation of application No. PCT/IL2007/001317, filed on Oct. 30, 2007.

(60) Provisional application No. 60/855,143, filed on Oct. 30, 2006.

(51) Int. Cl.
*A61B 5/02* (2006.01)

(52) U.S. Cl. ......... 600/485; 600/502; 600/504; 600/481

(58) Field of Classification Search .................. 600/310, 600/322, 323, 324, 502, 481, 485, 504
See application file for complete search history.

(56) References Cited

U.S. PATENT DOCUMENTS

| | | | |
|---|---|---|---|
| 5,058,596 A * | 10/1991 | Makino et al. | 600/476 |
| 5,598,841 A | 2/1997 | Taniji et al. | |
| 6,889,075 B2 * | 5/2005 | Marchitto et al. | 600/473 |
| 2004/0152989 A1 * | 8/2004 | Puttappa et al. | 600/473 |
| 2006/0063995 A1 | 3/2006 | Yodh et al. | |

OTHER PUBLICATIONS

International Search Report and Written Opinion, mailed Jun. 4, 2008, from International Application No. PCT/IL20071001317, filed Oct. 30, 2007.
EPO search report of EP 07827291 national phase of PCT/IL2007/001317 (related case in Europe)—mailed May 30, 2011.

* cited by examiner

*Primary Examiner* — Eric Winakur

(57) ABSTRACT

A system, method and medical tool are presented for use in non-invasive in vivo determination of at least one desired parameter or condition of a subject having a scattering medium in a target region. The measurement system comprises an illuminating system, a detection system, and a control system. The illumination system comprises at least one light source configured for generating partially or entirely coherent light to be applied to the target region to cause a light response signal from the illuminated region. The detection system comprises at least one light detection unit configured for detecting time-dependent fluctuations of the intensity of the light response and generating data indicative of a dynamic light scattering (DLS) measurement. The control system is configured and operable to receive and analyze the data indicative of the DLS measurement to determine the at least one desired parameter or condition, and generate output data indicative thereof.

23 Claims, 11 Drawing Sheets

SYSTEM AND METHOD FOR IN VIVO MEASUREMENT OF BIOLOGICAL PARAMETERS

RELATED APPLICATIONS

This application is a Continuation of International Application No. PCT/IL2007/001317, filed on Oct. 30, 2007, which in turn claims the benefit under 35 USC 119(e) of U.S. Provisional Application No. 60/855,143, filed on Oct. 30, 2006, both of which are incorporated herein by reference in their entirety.

FIELD OF THE INVENTION

The present invention relates to a system and method for in vivo measurement of biological parameters of a subject.

BACKGROUND OF THE INVENTION

Near infrared spectroscopy (NIRS) is a well-established non-invasive technique which allows for the determination of tissue and blood analytes conditions based on spectrophotometric measurements in the visible and near-infrared regions of the spectrum of light. According to this technique, incident light penetrates the examined skin, and reflected and/or transmitted light is/are measured. In order to quantify any blood analyte, light of at least two different wavelengths is required. Optical plethysmography, pulse oximetry, and occlusion spectroscopy are the most prominent examples of usage of the NIR spectroscopy in medicine and physiological studies.

Visible or near infrared light is commonly used to track the optical manifestation of some time-dependent physiological processes. Such prolonged measurement of light response as a function of time can provide clinician with valuable information about time-dependent physiological processes.

For example, the measured light response of a natural heart beat pulsation is varied with each pulse. The signal is then measured at one point of the pulse wave and compared with the signal at another point. The difference between the values is due to arterial blood alone. In the pulse-oximetry, this phenomenon is utilized for the determination of oxy-hemoglobin saturation.

In the case of occlusion spectroscopy, the optical time-dependent signal is originated by light scattering changes associated with the red blood cells (RBC) aggregation process. In this case, the optical signal changes are utilized for the hemoglobin or glucose measurement.

Yet another known method enables to generate the required changes is the application of a periodic or non-periodic local pressure variation, resulting in blood volume fluctuations. These fluctuations are used to measure different blood parameters, like hemoglobin or glucose.

The major underlying assumption in the processing of all kind of the time-dependent signals is that the measured optical variation is originated solely by blood related components. In pulse oximetry, for example, it's commonly accepted that arterial blood volume changes are the only responsible factor staying behind the optical signal modulation. However, a more complex physical analysis shows that even if the only changes in the system are ascribed to the blood, the measured optical response of these changes is a convolution of absorption and scattering properties of blood and surrounding media. While carrying out any algorithmic modeling and signal processing procedure of these measured optical signals, the tissue related effects can not be disregarded. Therefore, the common denominator of all time-dependent signal related optical methods relies on the measurement of optical responses originated by the blood dynamics or hemorheological status changes.

It should be noted that the accuracy of time-dependent methods depends on the ability to identify the hemorheological component of the blood. For example, in the particular case of pulse-oximetry, the heart beats modulate the hemorheological status of circulating blood, resulting in the fluctuation of RBC velocity, which is associated with the shear forces changes. The variation of the hemorheological blood parameters enables to optically distinguish the pulse-related changes of the signal. Therefore, the decreased accuracy in the determination of hemorheological properties leads to a lower accuracy in the determination of the sought blood parameter. Among the blood parameters which can be derived from the hemorheological changes are hemoglobin oxygen saturation, carohyhemoglobin (percentage of HbCO out of total hemoglobin), hemoglobin blood concentration and/or glucose.

Moreover, the arterial blood pressure is another physiological parameter, which is commonly derived from the hemorheological related variations. The systolic blood pressure can be determined with assistance of inflating cuff which induces hemorheological variations artificially. When a pressure beyond the systolic pressure is applied, no pulsatile waveform appears at the down-flow. The diastolic point of the pressure is frequently measured by using Korotkoff's sounds. The source of these sounds is associated with abrupt changes in hemorheological properties of blood, occurring due to deflation of cuff from the systolic point. These hemorheological changes, in the vicinity of the diastolic point, result in a very typical pattern of sound, which can be detected by a stethoscope or by other acoustic device. However, the sound related method is very sensitive to different motion artifacts and therefore in automatic blood pressure devices, commonly used for the self-monitoring, the accuracy of blood pressure reading is impaired.

SUMMARY OF THE INVENTION

There is a need in the art in facilitating in vivo measurements of rheological parameters of a subject, by providing a novel measurement technique. This is associated with the two major problems related to time-dependent optical methods for the measurement of hemorheological processes.

Firstly, the method of detecting hemorheological changes optically has a quite restricted sensitivity. Since the currently used method of optical measurement detects only scattering or absorption related changes of the signal, when the aggregation factor not vary, the scattering and absorption remain unchanged and hemorheological fluctuations remain unmeasured. For example, the measured optical signal has few ranges of low sensitivity with respect to the blood velocity changes. The limitation comes into force where the blood flow value is very high and, consequently, RBC aggregation process is prevented by very strong shear forces. Moreover, when the blood flow is very weak and the RBCs have already aggregated, the blood flow changes can not affect the aggregation status.

Secondly, in the currently used technique, there is a problem in the reduction of motion artifacts. Most of the motion artifacts interfering with time-dependent measurements are removed based on fact that the characteristic time constants are different from slow, motion related interferences. When the motion artifacts characteristic appearance is in the close vicinity to the signal appearance (for example, 1 Hz of the heart beat interference with 1.1 Hz of the bounce of the running person), the hemorheological signal is almost undistinguishable from the artifact.

The novel technique of the present invention enables to differentiate clearly between the blood-originated and tissue-related signals, reduce the problem of motion artifacts, determine at least one desired parameter or condition of a subject such as hemorheological (blood rheology) related parameters, for example apparent blood and blood plasma viscosity, red blood cells (RBC) aggregation, blood flow or blood coagulation properties, and based on these rheological parameters to determine chemical parameters of blood, such as oxygen saturation, hemoglobin, or glucose concentrations and physiological system parameters, like blood pressure and blood flow.

Moreover, there is a need in performing an accurate blood pressure measurement by measuring hemorheological properties changes optically, using more robust and noise resistant method.

As indicated above, the conventional techniques remove most of the motion artifacts interfering with pulse measurements, using characteristic time constants of heart beats which are different from slow motion related interferences. However, other types of motion artifacts interfering with pulse measurements, such as patient shivering, can not be removed by such techniques. This type of artifact is indistinguishable from the signal generated by pulse, due to the analogous characteristic time constants shared between pulse frequency and the frequency of the body shivering. Another example of indistinguishable motion artifact is associated with walking or running activities, where the characteristic frequencies of the motion pattern may overlap the heart rate frequency ranges. The last fact is considered as a great obstacle in utilization of the photoplethysmography or like for the heart rate measurements during the sport or walking activities.

The present invention solves the above problems by providing a novel optical technique suitable for the in vivo measurement in a subject utilizing dynamic light scattering (DLS) approach. More specifically, the present invention utilizes the effect of DLS for the measurement of variety of blood related parameters, like viscosity of the blood and blood plasma, blood flow, arterial blood pressure and other blood chemistry and rheology related parameters such as concentration of analyte (e.g. glucose, hemoglobin, etc.), oxygen saturation etc.

DLS is a well-established technique to provide data on the size and shape of particles from temporal speckle analysis. When a coherent light beam (laser beam, for example) is incident on a scattering (rough) surface, a time-dependent fluctuation in the scattering property of the surface and thus in the scattering intensity (transmission and/or reflection) from the surface is observed. These fluctuations are due to the fact that the particles are undergoing Brownian or regular flow motion and so the distance between the particles is constantly changing with time. This scattered light then undergoes either constructive or destructive interference by the surrounding particles and within this intensity fluctuation information is contained about the time scale of movement of the particles. The scattered light is in the form of speckles pattern, being detected in the far diffraction zone. The laser speckle is an interference pattern produced by the light reflected or scattered from different parts of an illuminated surface. When an area is illuminated by laser light and is imaged onto a camera, a granular or speckle pattern is produced. If the scattered particles are moving, a time-varying speckle pattern is generated at each pixel in the image. The intensity variations of this pattern contain information about the scattered particles. The detected signal is amplified and digitized for further analysis by using the autocorrelation function (ACF) technique. The technique is applicable either by heterodyne or by a homodyne DLS setup.

According to one broad aspect of the invention, it provides a system for use in non-invasive determination of at least one desired parameter or condition of a subject having a scattering medium in a target region. The system comprises an illuminating system including at least one source of partially or entirely coherent light to be applied to the target region in said subject to cause a light response signal from the illuminated region; a detection system including at least one light detection unit configured for detecting time-dependent fluctuations of the intensity of the light response and generating data indicative of the a dynamic light scattering (DLS) measurement; and, a control system configured and operable to receive analyze the data indicative of the DLS measurement to determine the at least one desired parameter or condition, and generate output data indicative thereof. The data generated by the detection system is indicative of fluctuation dependent speckle pattern of the light response over a predetermined frequency interval.

In some embodiments, the control system is configured and operable for analyzing the received data by using temporal autocorrelation intensity analyzing or power spectrum analyzing. The control system may be configured and operable analyze the received data, to reject low frequency component of the received data, and process high frequency components of the received data, thereby enabling elimination of motion artifacts. The control system comprises: a data acquisition utility responsive to the generated data coming from the detection system; a modulating utility associated with the illuminating system; a data processing and analyzing utility for analyzing data from the data acquisition utility and determine at least one hemorheological and blood chemical parameter; a memory utility for storing coefficients required to perform predetermined calculation by the data processing and analyzing utility, and an external information exchange utility configured to enable downloading of the processed information to an external user or to display it.

According to some embodiments of the invention, the system comprises a controllably operated pressurizing assembly configured and operable to affect a change in a blow flow, the control system comprising a control utility associated with the pressurizing assembly.

The system may comprise fiber optics for collecting the light response signal and delivering it to the detection system.

According to some embodiments of the invention, the system having at least two light sources operable at different wavelength ranges. The illuminating system is adapted to produce light of red and near infrared spectral regions, enabling assessment of the arterial blood oxygen saturation and/or in blood hemoglobin determination.

The system may be configured and operable to create an intermittent blood stasis state by applying over systolic blood pressure to the subject, thereby enabling the determination of red blood cell (RBC) aggregation.

In some embodiments, at least one light source of the illumination system is coupled with a polarization unit enabling to create polarized electromagnetic signal in one preferable direction. An entrance of at least one of detection units of the detection system is also coupled with a polarization unit, such that the polarization unit enables only certain direction of pre-selected polarized radiation to be detected increasing the signal to noise ratio.

According to another broad aspect of the invention, the present invention provides medical tool for carrying out non-invasive measurement and/or treatment on a patient's body. The medical tool comprises an illuminating system generating partially or entirely coherent light to be focused on a target region in the body, and a detection system configured for detecting time-dependent fluctuations of the intensity of the light response and generating data indicative of a dynamic light scattering (DLS) measurement.

According to yet another aspect of the invention, the present invention provides an optical method for use in determining in vivo hemorheological chemical and physiological parameters of a subject. The method comprises generating a partially or entirely coherent light; applying the light to a target region in the subject; detecting fluctuation dependent speckle pattern of the light response over a predetermined frequency interval and generating data indicative thereof; processing the detected data by using the temporal autocorrelation intensity analyzing or the power spectrum analyzing; and, determining at least one desired parameter or condition of the subject from the time-fluctuation of a dynamic light scattering (DLS) signal.

In some embodiments, the method comprises rejecting low frequency component of the detected DLS signal by using high-pass filters; and processing high frequency components to eliminate motion artifacts.

The chemical parameter comprises at least one of the following: a blood viscosity, an average size of RBC aggregates, and blood coagulation properties.

In some other embodiments, the method comprises creating temporal blood flow cessation at the measurement region to measure a post-occlusion signal. The method comprises analyzing the measured post-occlusion signal to determine blood plasma viscosity and a rate of RBC aggregation.

In some other embodiments, the method comprises illuminating the target region with light of red and near infrared spectra, thereby enabling for measuring simultaneously the DLS signal at two or more wavelengths to determine at least one of the following: arterial blood oxygen saturation, blood hemoglobin concentration, and glucose concentration.

According to yet another aspect of the invention, the present invention provides an optical method for determining in vivo arterial blood pressure of a subject. The method comprises applying partially or entirely coherent light to a target region in the subject to cause a light response signal from the target region; applying a controllable pressure to the subject so as to induce hemorheological variations artificially; detecting fluctuation dependent speckle pattern of the light response signal over a predetermined frequency interval and generating data indicative thereof; processing the detected data by using temporal autocorrelation intensity analyzing or power spectrum analyzing; and, determining systolic and diastolic arterial blood pressure values from the time-fluctuation of the DLS signal.

According to yet another aspect of the invention, the present invention provides an optical method for determining in vivo heart pulse rate of a subject. The method comprises applying a partially or entirely coherent light to a target region in the subject to cause a light response signal from the target region; detecting fluctuation dependent speckle pattern of the light response over a predetermined frequency interval, and generating data indicative thereof; processing the detected data by using temporal autocorrelation intensity analyzing or power spectrum analyzing; and, determining the heart rate pulsation from the heart beat time fluctuation of the DLS related parameter.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
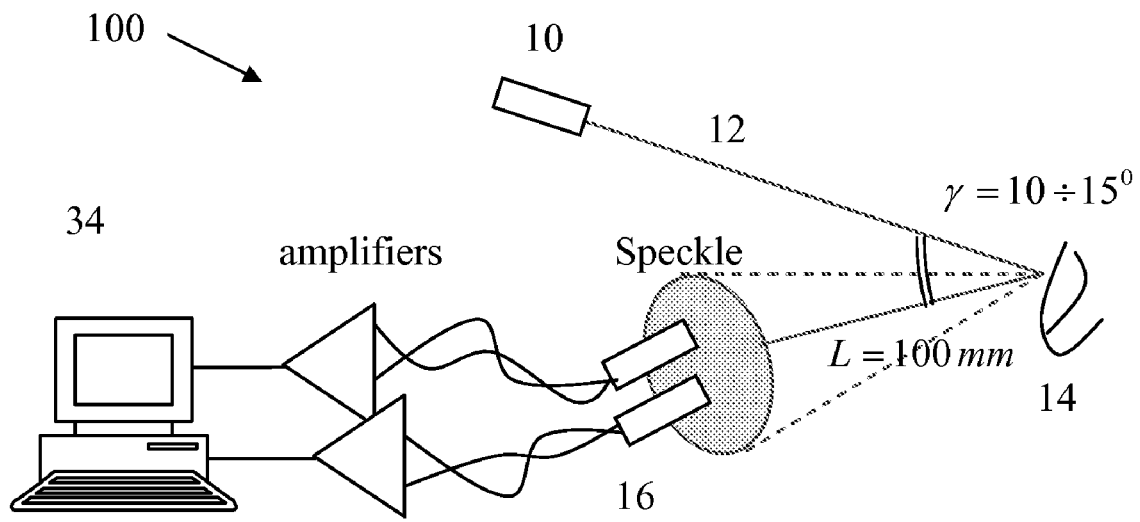
FIG. 1 is an illustration of a DLS measurement based system according to the teachings of the present invention.

Reference is made to FIG. 1 illustrating a DLS measurement based system 100 implementing the present invention. System 100 includes a light source unit 10 (e.g. laser) for generating at least partially coherent light; optical arrangement (not shown) including focusing optics and possibly also collecting optics; and a detection unit 16. A focused beam of light 12 produced by laser 10 (e.g., a He—Ne laser) is used as a localized light source. In a non-limiting example, a light source unit 10 may be a laser diode (650 nm, 5 mW) or VCSEL (vertical cavity surface emitting laser). The light response i.e. the reflected and/or transmitted light returned from the localized region of the subject's surface 14 (patient's finger in the present example) illuminated with the localized light source 10, can be collected in a determined distance L (in a non-limiting example, L=100 mm) either directly by a detector or via multimode fiber optics. In a non-limiting example, the multimode fiber optics may be a bifurcated randomized optical fiber where one optical entrance is connected to the detector and another one is optically coupled with the laser diode. In particular, as shown in FIG. 1, system 100 includes at least one laser diode 10 and at least one photodetector (photodiodes) 16 appropriately positioned in the reflection-mode measurement set-up.

Figure 2:
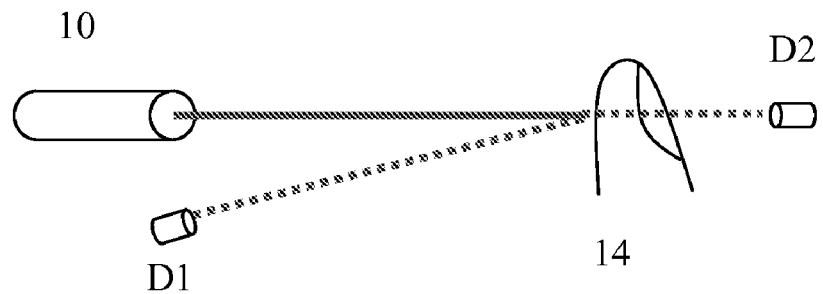
FIG. 2 is a schematic illustration of a simultaneous measurement of the transmission signal using photodetector D2 and of the reflection signal using photodetector D1.

As exemplified in FIG. 2, the system may be operable to implement simultaneous measurement of the transmission signal using photodetector D2 and reflection signal using photodetector D1. This can be used for a relatively transparent (for the respective wavelength range) subject (i.e. like through a subject's finger tip 14). It should be noted that generally, the system may be operable in either one of transmission and reflection modes or both of them.

Figure 3:
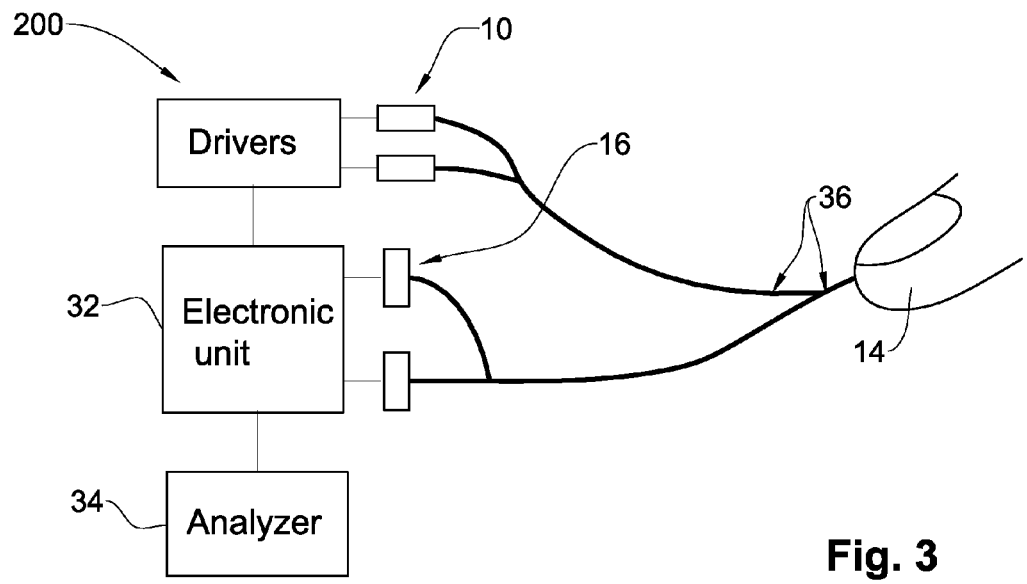
FIG. 3 is a schematic illustration of the use of an optical fiber-based system.

FIG. 3 exemplifies the use of an optical fiber-based system 200 having a somewhat different configuration. One of the advantages of optical fiber-based system 200 lies in the maximum flexibility of such system for non-invasive measurement of subjects. The use of randomized optical fiber secured geometric stability and the small effective distance between light source 10 and detector 16 is responsible for a high signal to noise ratio. It should be noted that the same fiber optic bundle 36 can be used for both the collection of the signal from the measured subject and the delivery of the coherent radiation towards the subject to be measured. Further provided is a control system having an electronic unit 32 and a data processor and analyzer (CPU) 34. The electronic unit 32 is configured and operable to reject a low frequency component of the detected signal by using high-pass analog filters, and process only high frequency components to strongly amplify them, digitize them, and pass to the control unit (CPU) 34 for further digital processing. This approach enables the required sensitivity and dynamic range to be increased which is essential to account for only DLS related component of the measured signal. In a non-limiting example, the data is collected at 22 KHz sampling rate and 16-bit resolution.

The kinetics of optical manifestations of two kinds of physiological signals is measured in vivo: the pulsatile signal associated with heart beats and the post-occlusion optical signal which is induced by an artificially generated blood flow cessation. The light transmission and/or reflection signals are used as a control of the physiological response. This kind of control measurement can be carried out simultaneously with the DLS reflection measurement. The mutual correspondence between DLS and standard optical signals is subject to a comparison analysis.

Figure 4:
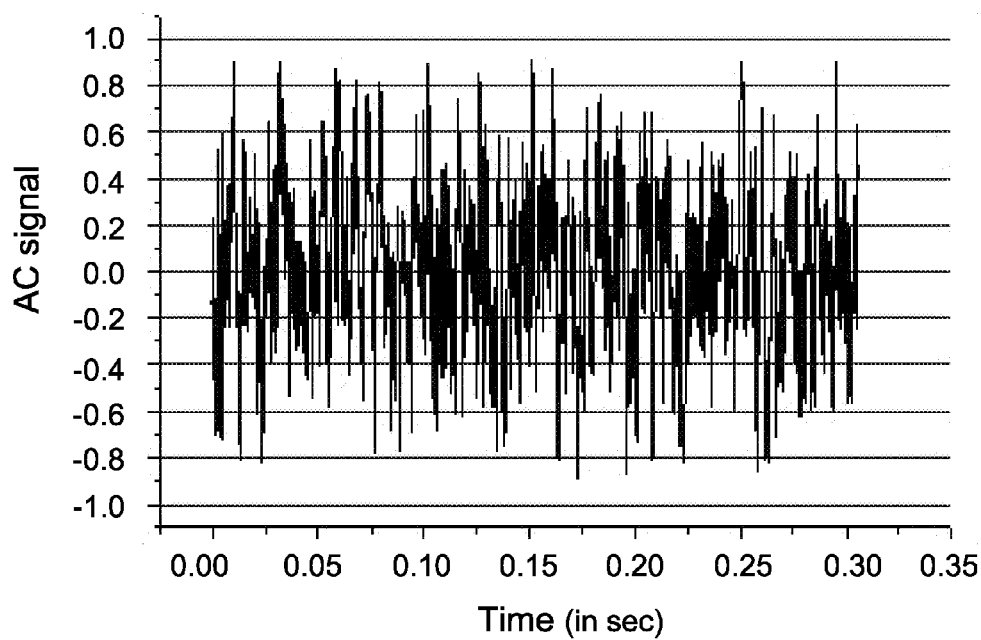
FIG. 4 is a graphical illustration of a raw data of pulse being collected and measured from the finger tip by the DLS system.

The following is an example of analysis of pulsatile and post-occlusion signals. Reference is made to FIG. 4 showing an example of raw data of pulse (AC signal variation with time) which is collected and measured from a finger tip by DLS system 100. The low frequency components of the signal are rejected by an analog filter of electronic box 32. Subsequently, the signal is amplified and digitized for further analysis.

Generally, two standard approaches are commonly applicable to an analysis of DLS signals. The first approach uses the temporal autocorrelation of the intensity, and the second approach entails the analysis of the power spectrum P(w) of the detected signal.

According to the first approach, the formula for the correlation function G(τ) of temporal intensity fluctuations of light scattered by moving particles is given by:

$$G(\tau) = \frac{\langle I(t) \cdot I(t+\tau) \rangle}{\langle I(t) \rangle^2} \quad [1]$$

where I(t) is the intensity at time t and < . . . > denotes an ensemble average. It has to be taken into consideration that for preferable configuration of measurement system 100, the intensity of the signal I(t) already lacks zero and low frequencies components of the signal (0-100 Hz), which are already removed by the high-pass analog filter of the electronic box 32.

When the measured signal is converted from an analog to digital form, the autocorrelation function is calculated by using a summation, averaging over N sampling points given by the following expression:

$$\langle G(\tau) \rangle = (1/N) \sum_{i=k}^{k+N} I(k) * I(k+i) / \sum I(k)^2 \quad [2]$$

Figure 5:
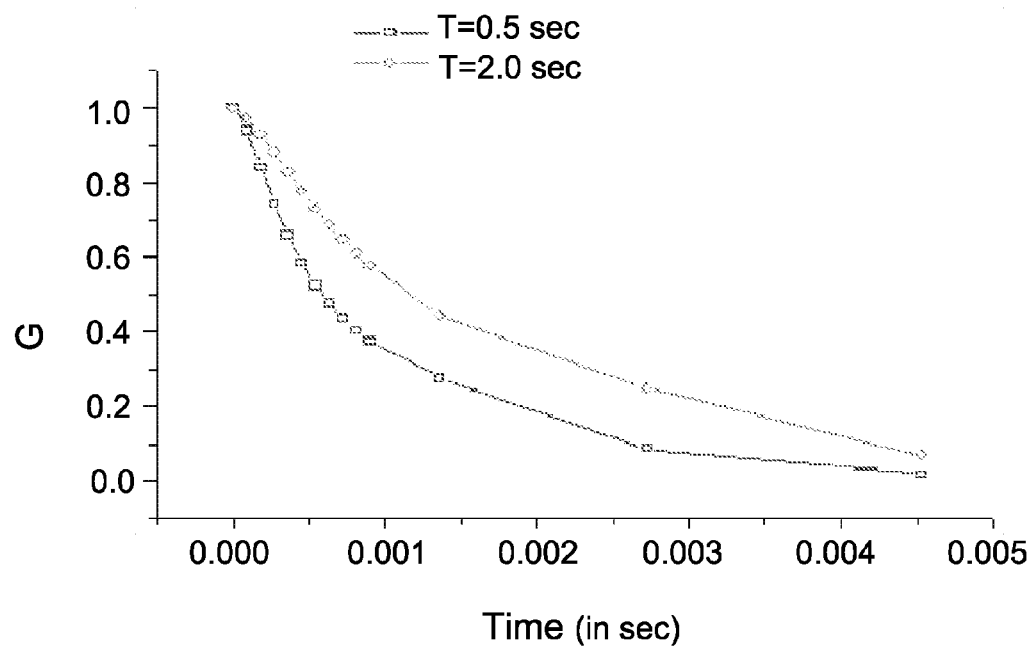
FIG. 5 is a graphical illustration of a change of a normalized function at measurement onset (0.5 sec) and after 20 sec of over systolic occlusion as measured on the finger tip by the DLS.

FIG. 5 shows a typical example of a normalized function G(τ) change as function of time and over systolic occlusion (20 sec occlusion vs 0.5 sec onset) as measured on the finger tip by DLS system 100. For the purpose of the present application, the term "over systolic occlusion" refers to an application of over systolic pressure to create a temporary blood flow cessation state at the measurement location. The first measurement onset (T=0.5 sec) displays a more fast decrease of G(t) in initial measurement stage (0-0.001 sec) comparatively to second measurement (T=20 sec) occlusion data. More moderate time-dependent decrease of G(t) is noticed for both experiments in more advanced stage (>0.001 sec)

Figure 6:
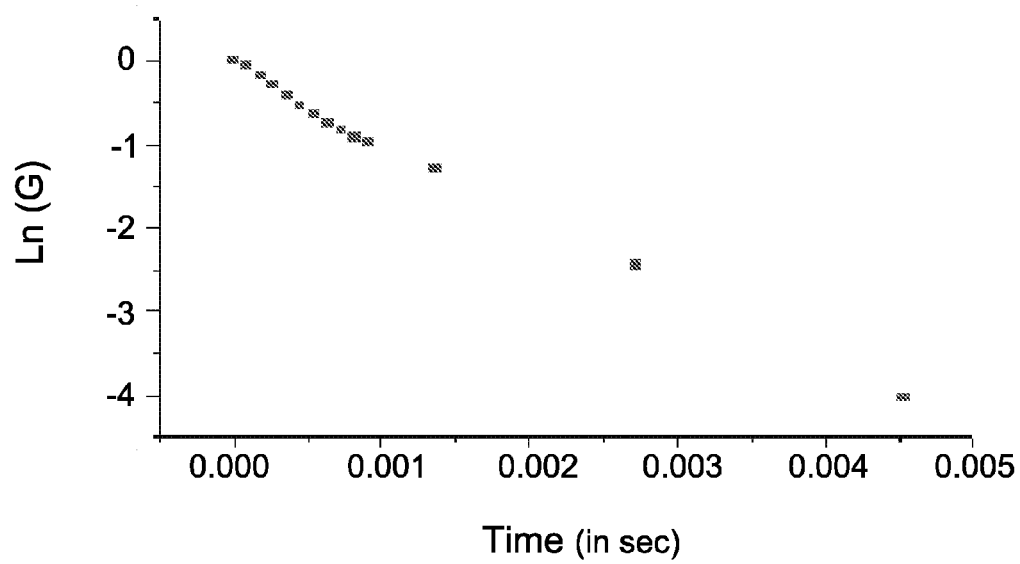
FIG. 6 is a logarithmic scale graphical presentation of the same.

The logarithmic scale presentation of the same represented in FIG. 6 reveals a quasi-exponential nature of function G(τ).

Figure 7:
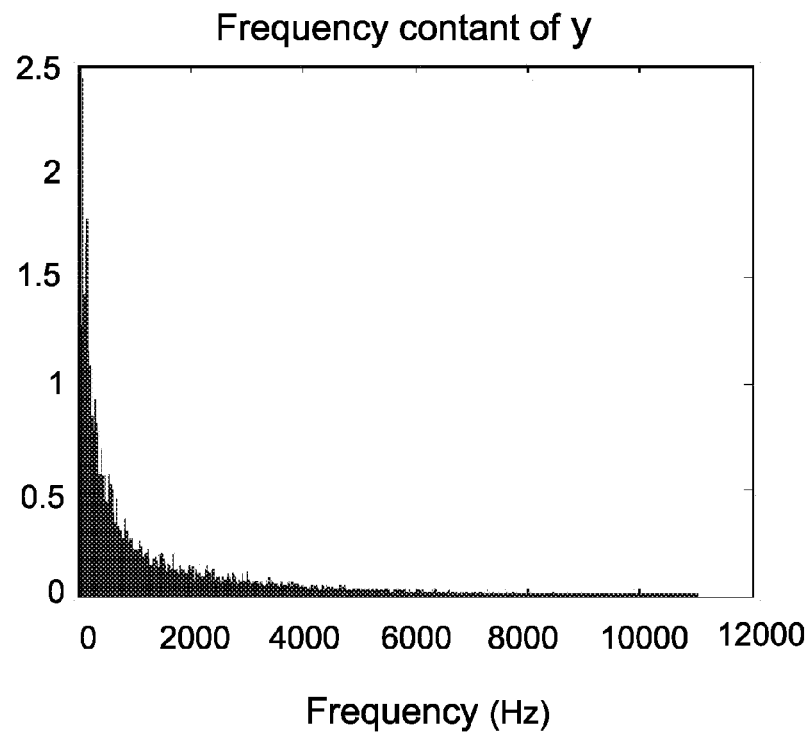
FIG. 7 is a graphical presentation of the power spectrum used to process the measured signal by using a standard Fast Fourier Transformation (FFT) digital signal processing algorithm.

According to the second approach, the power spectrum presentation is used to process the detected signal. The power spectrum of the measured signal can be constructed by using a standard Fast Fourier Transformation (FFT) digital signal processing algorithm. FIG. 7 shows an example of the FFT of such a signal. The highest spectral frequency in the FFT presentation is defined by the number of the sampling points and the overall measurement time interval. The total energy of a power spectrum PwS[f1,f2] is bounded in the frequencies interval (f1, f2) and can be evaluated by a simple summation. This value can be used as a measure of changes which occurs during any physiological processes during the blood flow or during the blood flow cessation.

Figure 8:
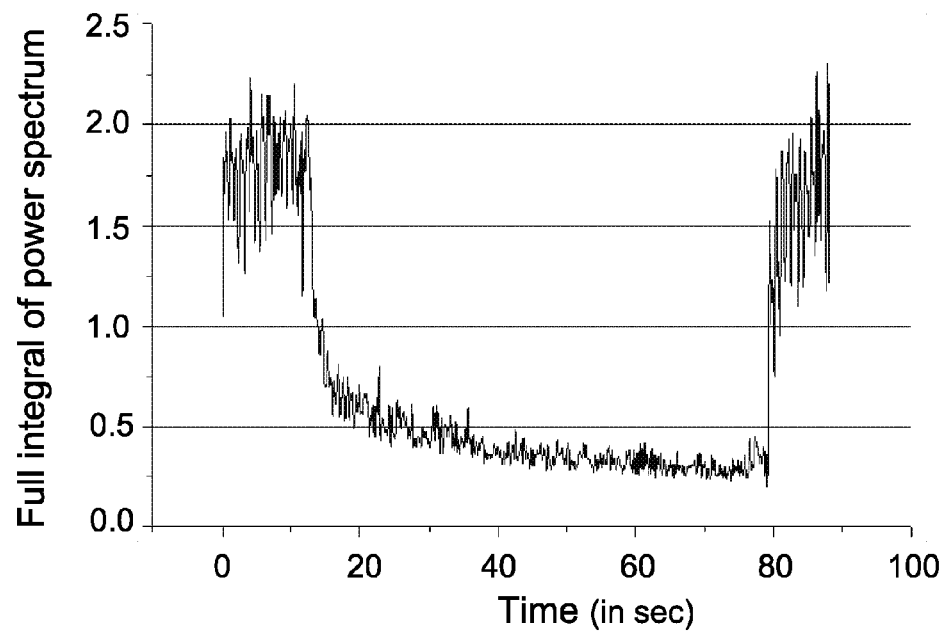
FIG. 8 is a graphical presentation of the time variation of the full integral of the power spectrum during an 80 sec duration measurement section, which is presented in terms of the energy power spectrum.

FIG. 8 shows the time variation of the full integral of the power spectrum (i.e. energy power spectrum) during an 80 sec duration measurement section of the pulsatile signal. Each point of the power spectrum PwS[f1,f2] is calculated for a pre-set time interval. In this particular example, the interval is 0.0454 sec. The calculated value is normalized:

$$PwS[f1, f2] = \sum_{f1}^{f2} PwS(f) \bigg/ \sum_{0}^{fmax} PwS(f) \qquad [3]$$

Figure 9:
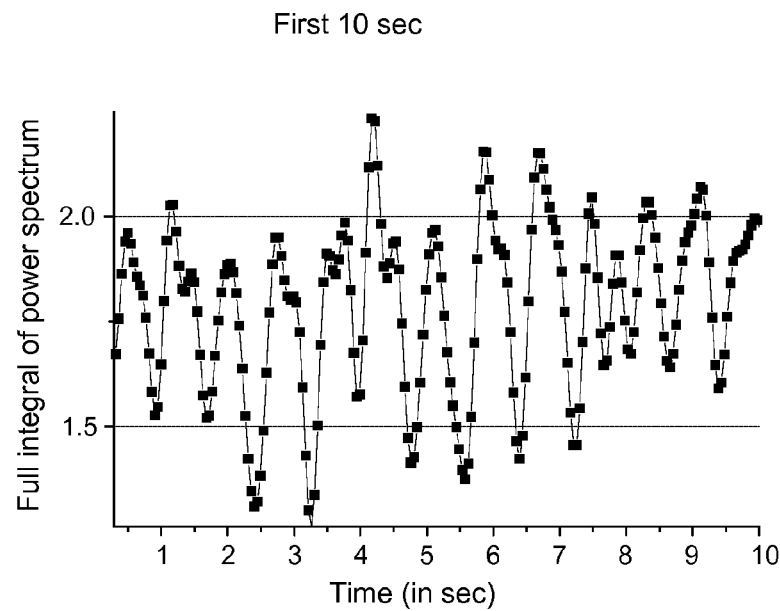
FIG. 9 is a graphical presentation of the time variation of the full integral of the power spectrum during the first 10 seconds of the pulsatile signal.
Figure 10:
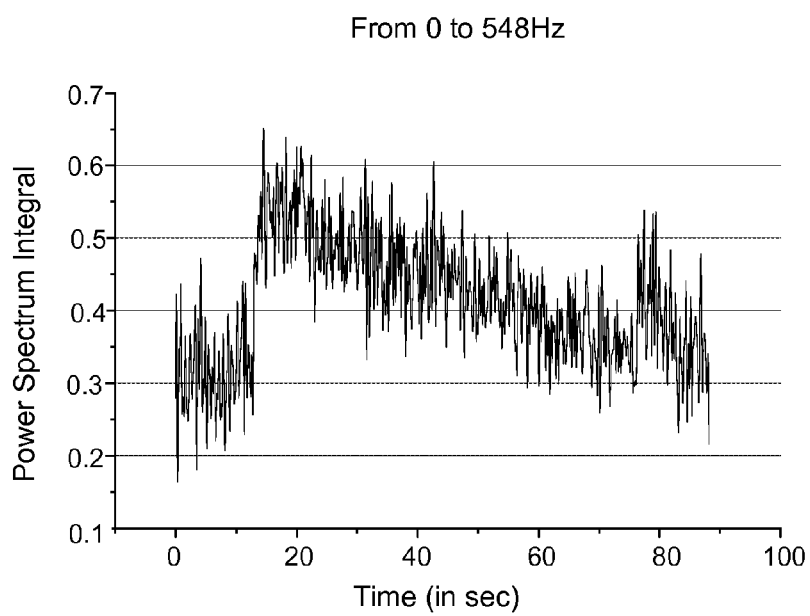
FIG. 10 is a graphical presentation of the power spectrum integral upon the frequency interval [0-550 Hz]
Figure 11A:
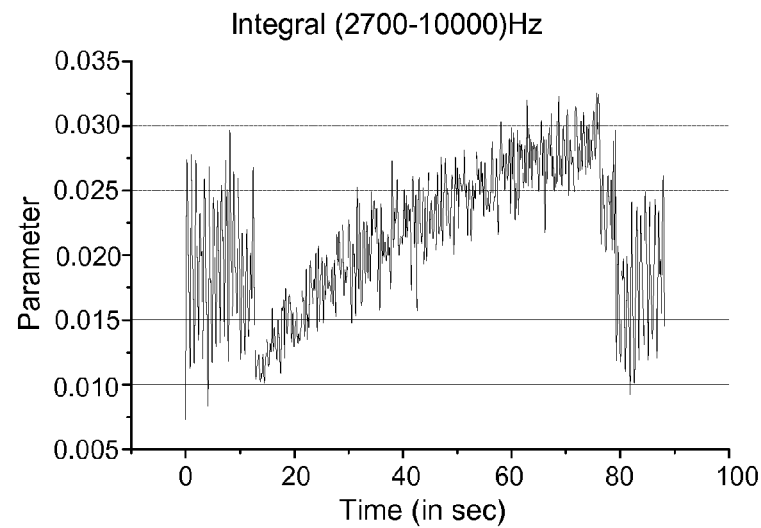
FIG. 11a-b are graphical presentations of the power spectrum integral upon the frequency interval [2700-10000 Hz]
Figure 11B:
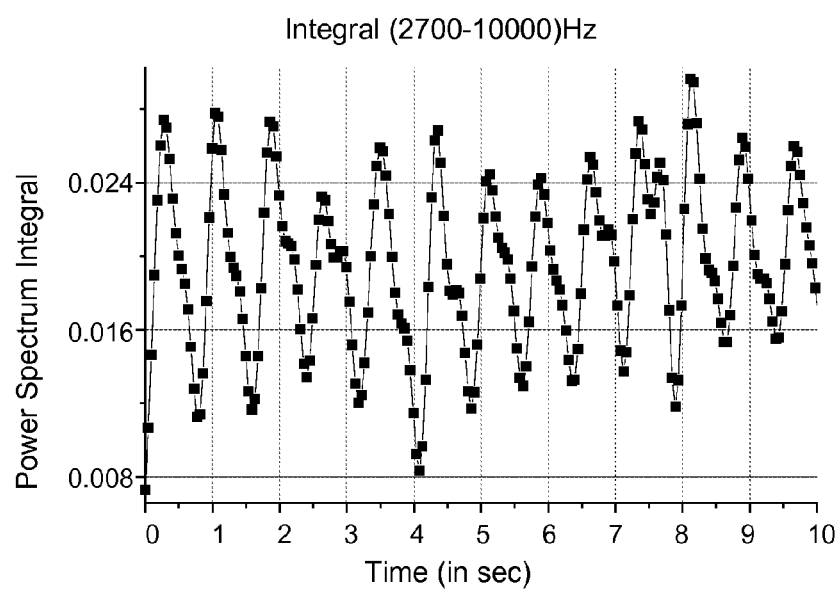
Figure 12:
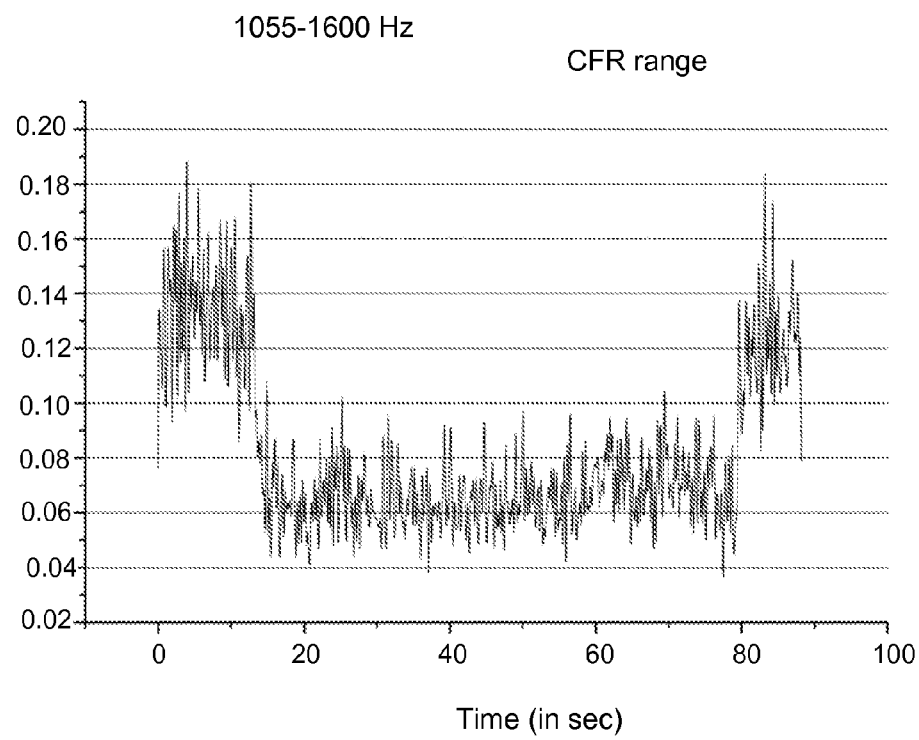
FIG. 12 is a graphical presentation of the power spectrum integral upon the frequency interval [1-1.6 KHz]

FIG. 9 shows the time variation of the full integral of the power spectrum during the first 10 seconds of the pulsatile signal. The characteristic behavior of the power spectrum PwS depends upon the frequency interval f1,f2. For example, referring to FIGS. 10 and 11a-b, the function defined by PwS [0,550 Hz] (t) for the frequency window [0,550 Hz], behaves differently as compared to PwS [2700, 10000 Hz] (FIG. 11a-b). Strong dependence of PwS function upon the chosen frequencies parameters is confirmed for the pulsatile phase, as illustrated in FIG. 11a and FIG. 11b. At a predetermined a frequency interval, PwS behaves as a very weak function of ongoing physiological scattering changes, as illustrated in FIG. 12. In this particular example, this interval is identified as being located at approximately the frequency interval [1-1.6 kHz]. This interval is defined as the critical frequency point (CFP), which can be related to the parameters of the autocorrelation function.

According to the statements of the Wiener-Khinchin theorem, PwS density of a wide-sense-stationary random process is the Fourier Transform of the corresponding autocorrelation function. Since the autocorrelation function is an even function, the classic Fourier integral is reduced to:

$$P(\omega, t) \approx \int_0^\infty \frac{\langle I \rangle^2}{2*\pi} \cos(\omega * \tau) * [g_2(\tau, t) - 1] * d\tau \qquad [4]$$

For a very simple case, the normalized intensity correlation function can be approximated to: $g_2(\tau) \approx \exp(-\alpha*\tau)$, where $\alpha$ is a factor proportional to the diffusion parameter D.

After the integration of the expression, [4] reduces to:

$$P \approx \frac{\alpha}{\alpha^2 + \omega^2} \qquad [5]$$

In order to find the minimum point of P, the differentiation of g with respect to $\alpha$ is taken:

$$d(P) = \left( \frac{-2\alpha^2}{(\alpha^2 + \omega^2)^2} + \frac{1}{\alpha^2 + \omega^2} \right) * d\alpha \qquad [6]$$

Therefore, $$\text{for } P(t)=0, \omega=\alpha \qquad [7]$$

According to this expression, CFP can be used to evaluate the diffusion parameter D.

Figure 13A:
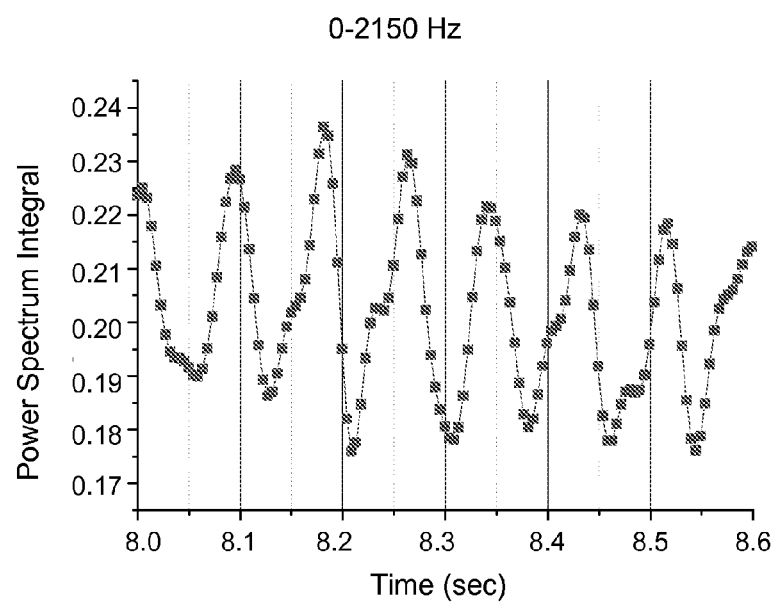
FIG. 13a is a graphical presentation of the power spectrum integral in the post-occlusion pulsatile sessions (80-86 sec) upon the frequency interval [0-2150 Hz]
Figure 13B:
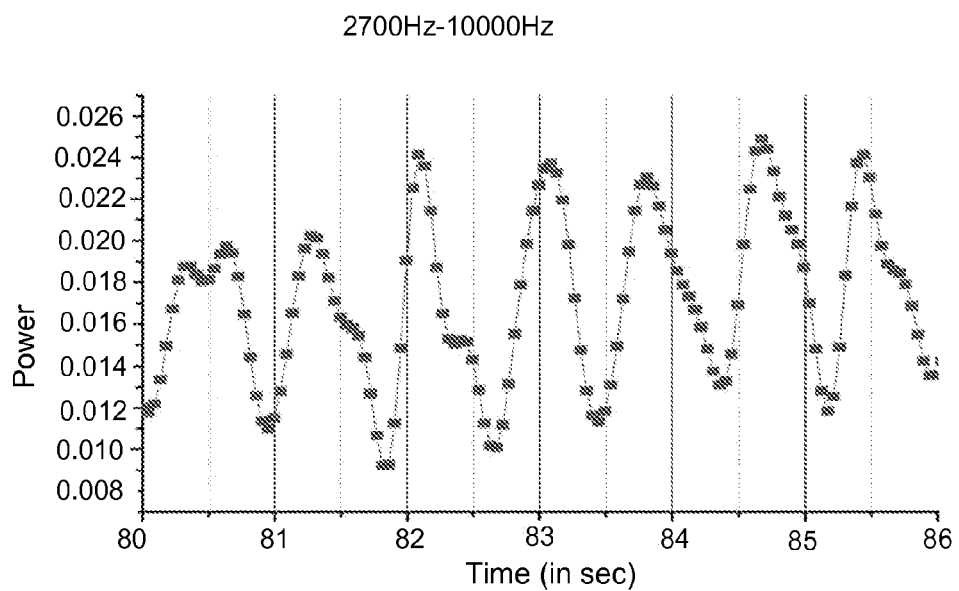
FIG. 13b is a graphical presentation of the power spectrum integral in the post-occlusion pulsatile sessions (80-86 sec) upon the frequency interval [2700-10000 Hz]

The post-occlusion pulsatile sessions (80-86 sec) are represented for the frequency window [0, 2150 Hz] in FIG. 13a, and for the frequency window [2700, 10000 Hz] in FIG. 13b.

Thus, the invented technique provides for using DLS for measurement of various parameters of a subject, particularly blood analytes. In this connection, it should be noted that the multiple scattering predominates the light propagation through the blood and tissue. This is why the transport approximation is considered to be a more appropriate approach for the invented technique.

In the case of DLS, the measured parameter is autocorrelation function $g_1$. For an infinite medium with a point source, this parameter can be approximated by:

$$g_1(\tau) = \exp(-\sqrt{k_0^2 * \langle \Delta r^2(\tau) \rangle + 3\mu_a l} * (r_{sd}/l)) \qquad [8]$$

where $\langle r^2(\tau) \rangle = 6D\tau$ is the mean squared displacement of the scattered particles, l is mean free path of light and D is the diffusion coefficient given by Stoke-Einstein relation.

$$D = \frac{kT}{3*\pi\eta d} \qquad [9]$$

Substitution of K and D into [8] gives:

$$g_1(\tau, \lambda) = \exp\left(-\sqrt{(2\pi n/\lambda)^2 * \frac{kT}{3*\pi\eta d} + 3\mu_a * l} * (r_{sd}/l)\right) \qquad [10]$$

It should be pointed out that $\mu_a$ is a function of light absorption dependent on the hemoglobin concentration and blood oxygen saturation level in blood. This expression can be used to process the DLS measurement of aggregation driven post-occlusion measurement where the Brownian motion takes over.

The value $g_1$ relates to the measured autocorrelation function by the Segert relation:

$$g_2(\tau) = 1 + \beta * |g_1|^2 \qquad [11]$$

In the case of a free pulsatile signal, the blood flow related phenomena are dominated by fluctuations of blood cells with a major contribution of red blood cells (RBC).

The autocorrelation function decay is governed by the velocity variations measured across the blood vessels. If V(L) is the standard deviation of velocity difference across the source width L, then decay time is defined by:

$$\tau_c \approx \frac{1}{dV(L)} \qquad [12]$$

The velocity difference of flowing blood is a function of its shear rate. This rate depends on variety of rheological parameters, such as blood viscosity or the actual size of flowing particles. Single RBC tends to form aggregates that can reversibly disaggregate under the influence of shear forces; RBC aggregation is a major determinant of the shear-thinning property of blood.

In a vessel of radius R, axisymmetric velocity profiles v(r,t) can be described in cylindrical coordinates by the empirical relationship:

$$v(r,t) \approx v_{max} * (1 - (r/R)^\xi) * f(t) \qquad [13]$$

where $-1 < (r/R) < 1$, f(t) is a periodic function of heart beat frequency, which is driven by systolic pressure wave and it is time phase-shifted with respect to the cardiac cycle, and ξ represents the degree of blunting. For example, in 30 micron arterioles, there is a range of ξ 2.4-4 at normal flow rates. If ξ=2, a parabolic velocity distribution is obtained. Blunting would occur even in larger arterioles at low flow rates. By using the expression for d(v(r,t)) the standard deviation d(v) can be calculated by:

$$rms(dV) = v_{max} * f(t) \sqrt{\frac{\int dv(r) * r^2 * dr}{\int dv(r) * dr}} = \frac{\xi * R^2}{2+\xi} * v_{max} * f(t) \quad [14]$$

For small arterials (around 20 microns), the fluctuation of velocity from systolic to diastolic phases ranges from 1.5 mm/s to 2.5 mm/s. This results in a very significant fluctuation of standard deviation (rms) during the systolic-diastolic cycle. Pulsatile signal, therefore, can be used for calculation of hemorheological parameters. The DLS related pulsatile signal is advantageous over regular pulse measurement where the motion artifacts are prevalent. In addition, it should be noted that hemorheological changes can be extracted optically even if the scattering or absorption related changes are negligible.

Therefore two major benefits are achieved: first, the pulsatile or other hemorheological change can be measured optically by using DLS-related technique; secondly, due to the process of only high frequency components in the DLS approach, low frequency interference is therefore eliminated, also eliminating motion artifacts.

Another hemorheological parameter relates to the blood plasma viscosity. The post-occlusion signal (which is achieved during the stasis stage) can be utilized to evaluate blood plasma viscosity. In this case, the particles are displaced in the blood by Brownian motion according to the Stoke-Einstein equation [9].

It is clear that for the post-occlusion signal, the observed changes in the DLS signal are driven by the growth rate of d(t), following the growth of RBC aggregate size. The rate of RBC aggregate growth can be defined by calculating the change of autocorrelation function occurring during the stage of blood flow cessation (post-occlusion stage). Therefore the rate of RBC aggregation can be measured by using this technique.

If the DLS signal is measured simultaneously at two or more wavelengths, then by using equation [10] or other such equations, the most influential scattering or absorption related parameters, such as oxygen blood saturation, hemoglobin or glucose can be determined since absorption properties of the scattering particles affect the DLS related parameters [10].

If the measurement system (e.g. system 100) includes a controllable pressurizing assembly, then the DLS effect can be used for measurement of arterial blood pressure. The point of systolic pressure is easily identified as a point of disappearance of the pulsatile signal, which is monitored either in terms of autocorrelation parameters or in terms of power spectrum. When the arterial pressure exceeds the cuff pressure, blood squirts through the partially occluded artery and creates turbulence, which creates the well-known Korotkoff sounds. Effect of turbulence results in dramatic change in fluctuation dependent speckle pattern which is expressed in an instant change of DLS parameters.

In many applications $\ln(G(\tau))$ can be approximated by a polynomial form:

$$G(\tau) = A\tau^2 + B\tau + C \quad [15]$$

Figure 14:
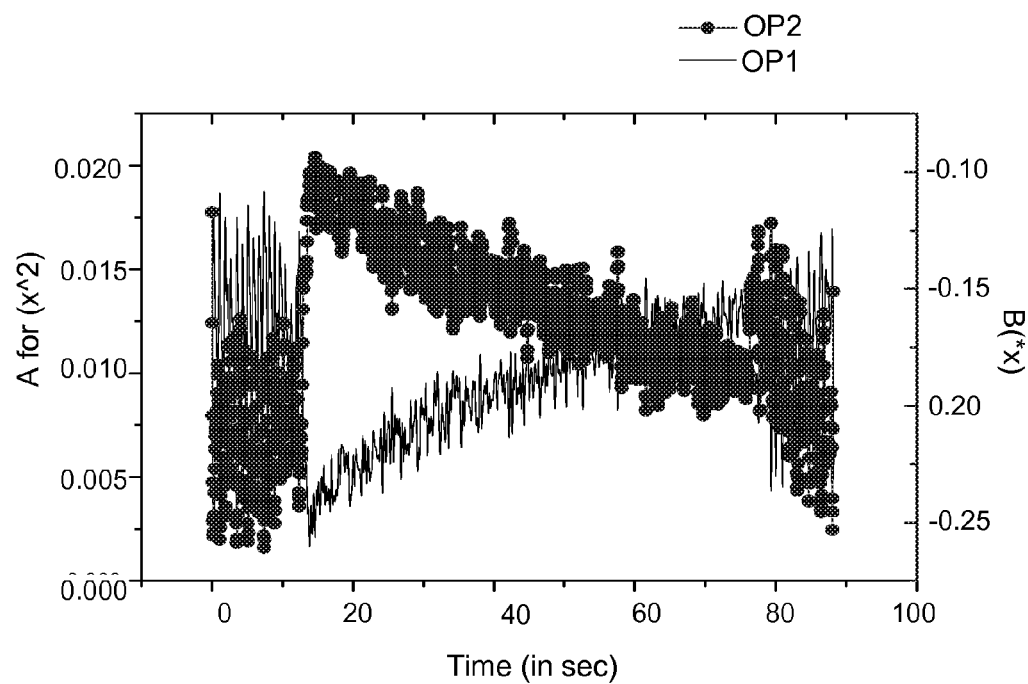
FIG. 14 is a graphical presentation of the pulsatile and post occlusion signals presented in terms of A(tn) and B(tn) of polynomial coefficients.

FIG. 14 illustrates how the pulsatile and post occlusion signals can be presented in terms of polynomial coefficients A and B being defined in terms of autocorrelation analysis. In this example, the measurement session includes few physiological stages: a) an initial pulsatile signal session, b) an arterial blood occlusion session, and c) a pulsatile signal session after release of the over systolic (occlusion) session, all over the measurement duration of 80 seconds.

Figure 15:
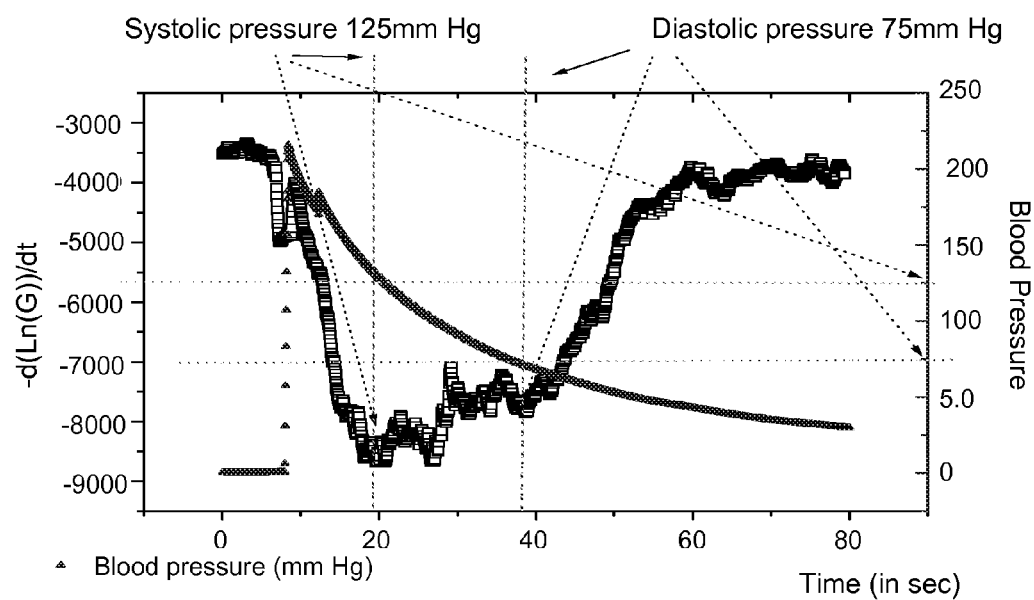
FIG. 15 is a graphical presentation of a DLS related parameter (d(ln(G)/dt)) utilized for the determination of systolic and diastolic blood pressure.

FIG. 15 shows the behavior of a DLS related parameter (d(ln(G)/dt)) utilized for the determination of systolic and diastolic blood pressure. In this experiment, the pressurizing cuff is inflated up to over systolic pressure of 200 mm Hg during the first 5 seconds. Thereafter, for the next 75 seconds, the air pressure in the cuff is gradually reduced. Simultaneously, the DLS measurement is carried out at the area beneath the cuff. It is clearly seen in FIG. 15, that the parameter d(Ln(G))/dt reaches its minimum point when the pressure measured in the cuff gets equal to the systolic pressure, as was defined previously by doing a standard blood pressure measurement test. Moreover, at the moment where the pressure in the cuff exceeds previously defined systolic pressure point, exactly at this point the value of parameter d(Ln(G))/dt starts to increase gradually. Therefore, by identifying these two extreme points on the curve of d(Ln(G))/dt, both systolic and diastolic blood pressure can be measured optically. Naturally, all other functions mathematically related to autocorrelation parameters, can be used for blood pressure measurement.

This very unique sensitivity of DLS related parameters to the blood flow can be used for identification of blood flow disturbances or even for blood stasis identification and verification. To this end, any kind of a medical tool such as intro-vascular catheter (e.g. used for angioplasty) can be linked with DLS equipped optical fiber. Such a system is very efficient for identification of plugs and blood vessels abnormalities disturbing the normal blood flow.

Moreover, blood circulation parameters measured by DLS technique can by embedded as an inherent part of new emerging technology of biofeedback. Based upon the biofeedback technique, different body parameters including the blood flow that can be beneficial to control emotional status, cardiovascular training, rehabilitation and other purposes can be controlled. For example, such a system can be used for the control of blood flow during recovery from heart failure. In the biofeedback applications, DLS based measurement system can be combined with facilities affecting the mental status of a subject. For example, a method of binaural beats can be used. The binaural beats are resulted from the interaction of two different auditory impulses, originating in opposite ears. The binaural beat is not heard but is perceived as an auditory beat and theoretically can be used to entrain specific neural rhythms through the frequency-following response (FFR), i.e. the tendency for cortical potentials to entrain to or resonate at the frequency of an external stimulus. Thus, a consciousness management technique can be utilized to entrain a specific induction of sympathetic and parasympathetic system. More specifically, biofeedback system based on the methods of binaural beats can be governed by the parameters of flowing blood measured by means of DLS.

There is also provided a method to select appropriate frequencies characteristics of the binaural beats, according to the optimization curve of peripheral blood parameters, which are tightly associated with a stage of maximum relaxation.

EXAMPLES

Various examples were carried out to prove the embodiments claimed in the present invention. Some of these experiments are referred hereinafter. The examples describe the manner and process of the present invention and set forth the best mode contemplated by the inventors for carrying out the invention, but are not to be construed as limiting the invention.

Example 1

To develop an optimized experimental approach for non-invasive visualization of blood clotting in vivo, an experimental protocol which allows visualizing fine changes in RBC motion at high spatial and temporal resolution, deep inside the tissue was established.

The experiments were performed on occluded blood vessels and detection was carried out by modification of DLS described above. Anesthetized animal (nude mice) were placed on the stage of a setup for intravital microscopy. Temporal over systolic occlusion was created by using a mechanical occluder which produces local mechanical pressure on the area of visibly large arteries within the mouse ear. The duration of the occlusion did not exceed 10 minutes.

In the first set of experiments, the illuminated area was imaged via a microscope by a CCD camera. The exposure time T of the CCD was 50 ms. Images were acquired through easy-control software at 20 Hz. The optical design of the system allowed for simultaneous laser irradiation and observation of a process of blood clotting via usage of a short pass optical filter (450 nm) placed in front of the CCD camera.

It was observed that mechanical occlusion of major blood vessels never leads to complete blood flow stasis in microvessels. Even after maximal occlusion, RBCs continued to move and the character of such motions was not stochastic. RBCs were moving for up to 1 hour after animals were euthanized. Therefore the absence of RBC motion in an occluded vessel can be a sign of blood clotting in vivo since polymerized fibrin can prevent even minimal movements of RBCs.

Example 2

In order to monitor the blood clotting process, as well as to solve the problem of light scattering by skin and tissue, DLS from laser light was used for imaging the fine changes in RBC motion inside occluded vessels through the skin of the mouse ear. Particularly in the second set of experiments, the same animal model and procedures for animal care as described above were used.

A diode laser (670 nm, 10 mW) was coupled with a diffuser, which was adjusted to illuminate the area of a mouse ear. The illuminated area was imaged through a zoom stereo microscope by a CCD camera. The exposure time T of the CCD was 50 ms. Images were acquired through easy-control software at 20 Hz. DLS imaging of RBC motion in occluded microvessels was based on the temporal contrast of intensity fluctuations produced from laser speckles that reflected from mouse tissue.

The temporal statistics of time integrated speckles was utilized in order to obtain a two-dimensional velocity map which represents blood vessels under flow and no-flow conditions. The value of the laser temporal contrast $K_t$ at pixel (x,y) was calculated based on the following formula:

$$K_t(x,y) = \sigma_{x,y} / \langle I_{x,y} \rangle$$

Where $I_{x,y}(n)$ is the CCD counts at pixel (x,y) in the $n^{th}$ laser speckle image, N is the number of images acquired and $\langle I_{x,y} \rangle$ is the mean value of CCD counts at pixel (x,y) over the N images.

Figure 16:
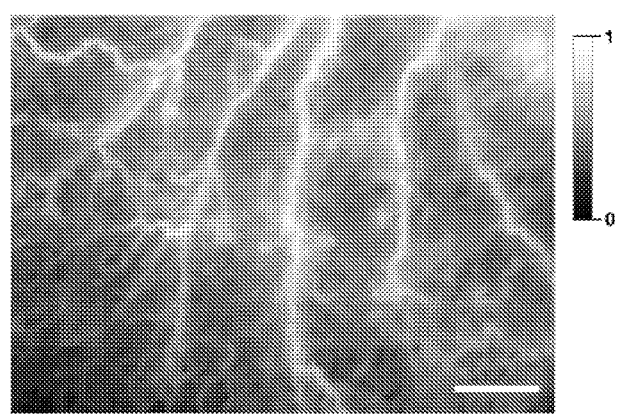
FIG. 16 is an imaging of a laser temporal speckle contrast $K_t$ inside occluded blood vessels.

Temporal mechanical blood occlusion in the observed area was applied, as described before, to ensure blood flow cessation. Referring to FIG. 16, the laser temporal speckle contrast $K_t$ was higher (intensity scale 0-1 in the right side of the image refers the value of laser speckle temporal contrast) inside occluded blood vessels in which RBC motion can be detected. These vessels are represented by "white" pattern while the darker areas are referred to the blood vessels in which RBC motion was low or negligible.

Figure 17:
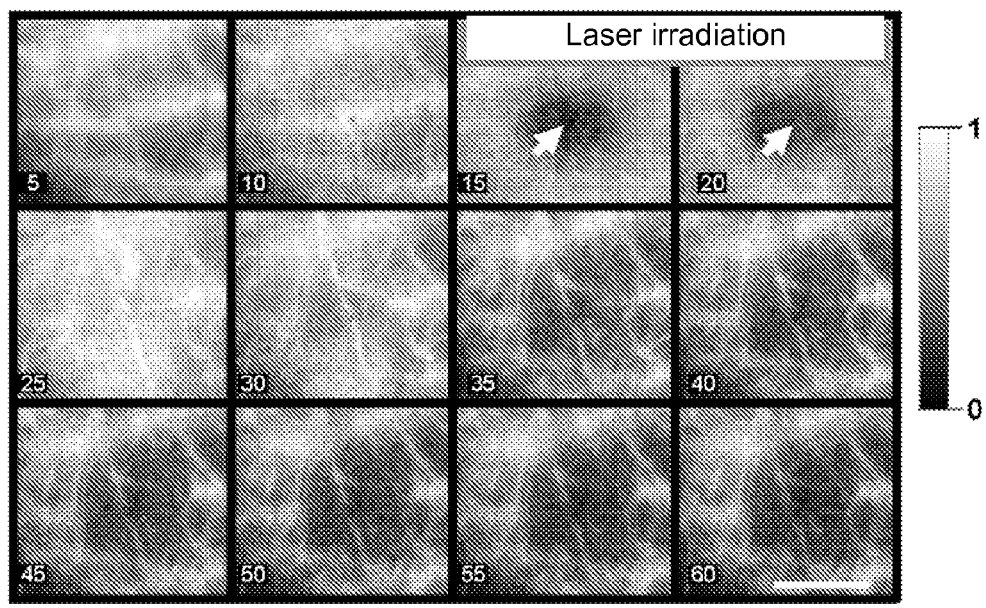
FIG. 17 is an imaging of a laser temporal speckle contrast $K_t$ inside occluded blood vessels and laser irradiation.

In addition, two minutes after occlusion, the beam of a Diode Pumped Solid State (DPSS) laser module, (Laser-Glow, Canada, 532 nm, 100 mW) was directed (at an angle of 45 degrees or less) onto the ear of an anesthetized mouse. The laser was focused in order to create a pinpoint injury on the mouse ear (200 μm). The injury was induced with a short high intensity laser burst and laser injury was induced at the area indicated by white arrows in frames 15s and 20s. The "white" pattern of blood vessels during DLS imaging, as illustrated in FIG. 17 of occluded blood vessels in the mouse ear can be related to remaining RBC motion. Conversely, relative changes in the intensity of $K_t$ upon clotting can be caused by elevation of blood/plasma viscosity as a result of blood clotting.

In the experiments, two elements of Virchow's triad were used to induce the process of clotting in vivo and to assess it optically. Both changes in the vessel wall, as well as in the pattern of blood flow, predispose the area to vascular thrombosis and blood clotting. Thus, DLS images generated by RBC motion inside occluded blood vessels as a marker of the blood clotting process in vivo were used.

Example 3

Figure 18:
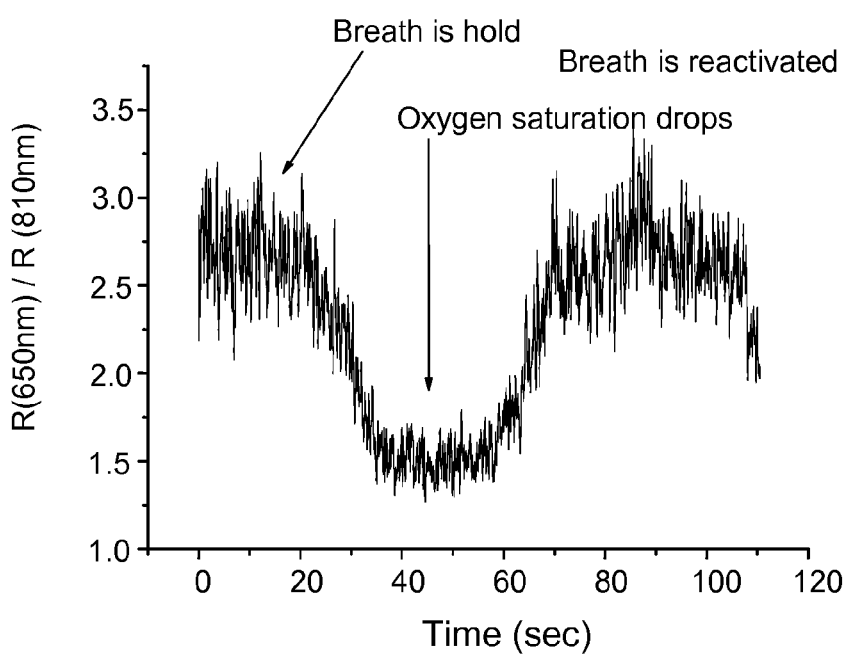
FIG. 18 is a graphical presentation of a DLS measurement utilized for the determination of the oxygen saturation changes; and, FIG. 19 is a graphical presentation of the measured pulsatile component of the blood in terms of d(ln(AUT)/dτ.

In order to monitor the change of oxygen saturation, a DLS system having two light sources was used. The light sources have respectively a wavelength of 650 nm and 810 nm. Absorption at these wavelengths differs significantly between oxyhemoglobin and its deoxygenated form, therefore from the ratio of the absorption of the red and infrared light the oxy/deoxyhemoglobin ratio can be calculated. The ratio of the two autocorrelation parameter (R1, R2) for each wavelength was measured. The patient was asked to hold hit breath for approximately 30 seconds. As illustrated in FIG. 18, the oxygen saturation drops. Then, the breath was reactivated, illustrated by a restoration of the oxygen saturation. The graph demonstrates the behavior of ratio of R1/R2 during this experiment and reveals good correspondence between the ratio and the induced change of oxygen saturation.

Example 4

By using the DLS related technique of the present invention, heart rate can also be measured. In this experiment, the method was tested on an upper wrist. This particular area is considered as a hardly available area for the commonly used photoplethysmographic method of pulse measurement. The pulsatile component in the wrist area is very weak and therefore is not used nor for heart rate measurement neither for pulse oximetry.

A special probe including a coherent light source (VCSEL (vertical cavity surface emitting laser) of 820 nm), a detection unit, a laser driver and a preamplifier probe was constructed. The detection unit was located in close vicinity of the light source. All this system was encapsulated in the enclosure having a wristwatch form. This "wristwatch" was closely attached to the wrist and the measurement has been carried out. The DLS signal reflected from the skin area has been detected, amplified and digitized at the rate of 40 KHz. The obtained results have been processed. The auto-correlation function (AUT) was determined and averaged over 0.05 sec and the slope of the logarithm of AUT as a function of $\tau$ (sampling rate) was calculated. $(d(\ln(AUT)/d\tau))$.

Figure 19:
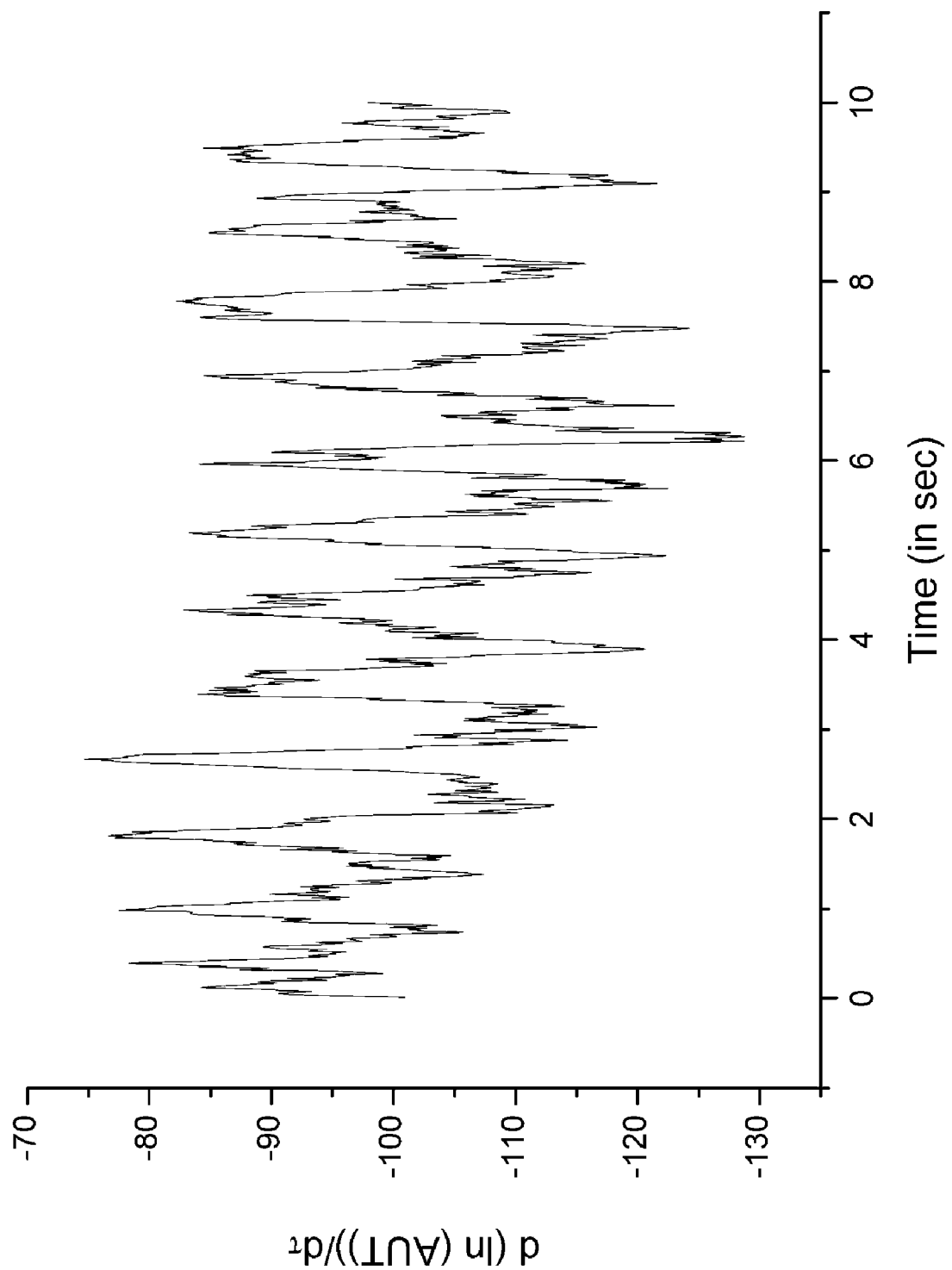

FIG. 19 represents the measured pulsatile component of the blood in terms of $d(\ln(AUT)/d\tau$. Heart rate is extracted from the obtained signal by utilizing any of commonly used methods such as FFT method.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for use in non-invasive in vivo determination of at least one desired parameter or condition of a subject having a scattering medium in a target region, said system comprising: (i) an illuminating system including at least one source of partially or entirely coherent light to be applied to the target region in said subject to cause a light response signal from the illuminated region; (ii) a detection system including at least one light detection unit configured for detecting time-dependent fluctuations of the intensity of the light response and generating data indicative of a dynamic light scattering (DLS) measurement; (iii) a control system configured and operable to receive and analyze the data indicative of the DLS measurement to determine said at least one desired parameter or condition, and generate output data indicative thereof; and a controllably operated pressurizing assembly configured and operable to affect a change in a blow flow.

2. The system of claim 1, wherein the data generated by the detection system is indicative of fluctuation dependent speckle pattern of the light response over a predetermined frequency interval.

3. The system of claim 2, wherein the control system is configured and operable for analyzing the received data by using temporal autocorrelation intensity analyzing or power spectrum analyzing.

4. The system of claim 1, wherein said control system is configured and operable to analyze the received data to reject low frequency components of the received data, and process high frequency components of the received data, thereby enabling elimination of motion artifacts.

5. The system of claim 1, wherein said control system comprises: a data acquisition utility responsive to the generated data coming from said detection system; a data processing and analyzing utility for analyzing data from said data acquisition utility and determine the at least one hemorheological and blood chemical parameter; a memory utility for storing coefficients required to perform predetermined calculation by said data processing and analyzing utility, and an external information exchange utility configured to enable downloading of the processed information to an external user or to display it.

6. The system of claim 5, wherein the control system comprises a control utility associated with the pressurizing assembly.

7. The system of claim 1, configured and operable to create an intermittent blood stasis state by applying over systolic blood pressure to the subject, thereby enabling determination of red blood cell (RBC) aggregation.

8. The system of claim 1, wherein said at least one light source of the illumination system is coupled with a polarization unit enabling to create polarized electromagnetic signal in one preferable direction, and an entrance of at least one of detection units of the detection system is coupled with a polarization unit such that the polarization unit enables only certain direction of pre-selected polarized radiation to be detected.

9. An optical method for use in determining in vivo hemorheological chemical and physiological parameters of a subject, the method comprising: (i) applying partially or entirely coherent light to a target region in said subject to cause a light response signal from the target region; (ii) detecting fluctuation dependent speckle pattern of the light response signal over a predetermined frequency interval, and generating data indicative thereof, (iii) processing the detected data by using temporal autocorrelation intensity analyzing or power spectrum analyzing; and, (iv) determining blood viscosity of said subject from the time-fluctuation of a dynamic light scattering (DLS) signal.

10. The method of claim 9, comprising: (i) rejecting low frequency components of the detected DLS signal by using high-pass filters; and (ii) processing high frequency components to eliminate motion artifacts.

11. An optical method for use in determining in vivo hemorheological chemical and physiological parameters of a subject, the method comprising: (i) applying partially or entirely coherent light to a target region in said subject to cause a light response signal from the target region; (ii) detecting fluctuation dependent speckle pattern of the light response signal over a predetermined frequency interval, and generating data indicative thereof, (iii) processing the detected data by using temporal autocorrelation intensity analyzing or power spectrum analyzing; and, (iv) determining at least one desired parameter or condition of said subject from the time-fluctuation of a dynamic light scattering (DLS) signal, wherein the method comprises creating temporal blood flow cessation at the measurement region to measure a post-occlusion signal.

12. The method of claim 11, comprising analyzing the measured post-occlusion signal to determine blood plasma viscosity.

13. A method of carrying out a non-invasive pulse rate measurement of a subject having a scattering medium in a target region, said system comprising:
    illuminating a target region in said subject by partially or entirely coherent light so as to cause a light response signal from the illuminated region;
    subjecting the light response signal to a dynamic light scattering measurement (DLS) by analyzing temporal fluctuations of speckle patterns of the light response signal; and
    computing, from the results of analysis of the temporal fluctuations of the speckle patterns of the DLS measurement, a pulse rate of the subject,
    wherein:
    i. the analysis includes computing a parameter whose value is approximately inversely proportional to the shear rate of the flowing blood; and
    ii. the pulse rate is derived from the value of the computed parameter.

14. The method of claim 13 wherein the parameter is the autocorrelation function decay time parameter.

15. The method of claim 13 wherein the parameter is a decay time parameter of an autocorrelation function of an intensive of the light response signal.

16. A method of carrying out a non-invasive pulse rate measurement of a subject having a scattering medium in a target region, said system comprising:

illuminating a target region in said subject by partially or entirely coherent light so as to cause a light response signal from the illuminated region;

subjecting the light response signal to a dynamic light scattering measurement (DLS) by analyzing temporal fluctuations of speckle patterns of the light response signal;

and computing, from the results of analysis of the temporal fluctuations of the speckle patterns of the DLS measurement, a pulse rate of the subject, wherein the analyzing includes processing the light signal with a band pass filter so as to compute a power frequency integral upon the frequency interval having an upper and lower bounds.

17. The method of claim 16 wherein the lower bound of the power frequency interval is about 2700 Hz.

18. The method of claim 17 wherein the upper bound of the power frequency interval is about 10,000 Hz.

19. The method of claim 16 wherein the upper bound of the power frequency interval is about 10,000 Hz.

20. A method of non-invasive in vivo determination of at least one desired parameter or condition of a subject having a scattering medium in a target region, the method comprising:

illuminating a target region in said subject by partially or entirely coherent light so as to cause a light response signal from the illuminated region, the light response signal having time fluctuations in a scattering intensity thereof due to changes in distances between blood particles;

detecting time-dependent fluctuations of the intensity of the light response signal to identify patterns descriptive of the changes in the distances between blood particles;

generating from the identified patterns, data indicative of a dynamic light scattering (DLS) measurement; and analyzing the data indicative of the DLS measurement to determine said at least one desired parameter or condition, the parameter or condition being related to the changes in distances between the blood particles wherein the desired parameter or condition is a systolic and diastolic blood pressure.

21. An optical method for use in determining in vivo hemorheological chemical and physiological parameters of a subject, the method comprising: (i) applying partially or entirely coherent light to a target region in said subject to cause a light response signal from the target region; (ii) detecting fluctuation dependent speckle pattern of the light response signal over a predetermined frequency interval, and generating data indicative thereof; (iii) processing the detected data by using temporal autocorrelation intensity analyzing or power spectrum analyzing; and, (iv) determining an average size of RBC aggregates of said subject from the time-fluctuation of a dynamic light scattering (DLS) signal.

22. An optical method for use in determining in vivo hemorheological chemical and physiological parameters of a subject, the method comprising: (i) applying partially or entirely coherent light to a target region in said subject to cause a light response signal from the target region; (ii) detecting fluctuation dependent speckle pattern of the light response signal over a predetermined frequency interval, and generating data indicative thereof; (iii) processing the detected data by using temporal autocorrelation intensity analyzing or power spectrum analyzing; and, (iv) determining blood coagulation properties of said subject from the time-fluctuation of a dynamic light scattering (DLS) signal.

23. An optical method for use in determining in vivo hemorheological chemical and physiological parameters of a subject, the method comprising: (i) applying partially or entirely coherent light to a target region in said subject to cause a light response signal from the target region; (ii) detecting fluctuation dependent speckle pattern of the light response signal over a predetermined frequency interval, and generating data indicative thereof; (iii) processing the detected data by using temporal autocorrelation intensity analyzing or power spectrum analyzing; (iv) creating temporal blood flow cessation at the measurement region to measure a post-occlusion signal and, (v) determining a rate of RBC aggregation of said subject from the time-fluctuation of a dynamic light scattering (DLS) signal by analyzing the measured post-occlusion signal to determine a rate of RBC aggregation.

* * * * *